US007607098B2

(12) United States Patent
Grehlinger et al.

(10) Patent No.: US 7,607,098 B2
(45) Date of Patent: Oct. 20, 2009

(54) SYSTEM AND METHOD FOR DYNAMICALLY CONTROLLING OPERATION OF RHEOMETRIC INSTRUMENTS

(75) Inventors: Peter Mark Grehlinger, Allentown, NJ (US); Ronald F. Garritano, Monroe Township, NJ (US); John P. Berting, Wilmington, DE (US)

(73) Assignee: Waters Investments Limited, New Castle, DE (US)

( * ) Notice: Subject to any disclaimer, the term of this patent is extended or adjusted under 35 U.S.C. 154(b) by 1082 days.

(21) Appl. No.: 10/643,879

(22) Filed: Aug. 20, 2003

(65) Prior Publication Data

US 2004/0177678 A1 Sep. 16, 2004

Related U.S. Application Data

(60) Provisional application No. 60/454,346, filed on Mar. 14, 2003.

(51) Int. Cl.
*G06F 3/00* (2006.01)
*G01N 11/00* (2006.01)
(52) U.S. Cl. .................. 715/762; 715/763; 715/771; 715/825; 73/54.01; 73/54.07
(58) Field of Classification Search .......... 715/763, 715/967, 825, 826, 771, 762–765; 73/54.01, 73/54.07
See application file for complete search history.

(56) References Cited

U.S. PATENT DOCUMENTS 6,173,438 B1  1/2001  Kodosky et al.

| 6,473,707 | B1 * | 10/2002 | Grey | .......................... 702/123 |
| 6,484,566 | B1 * | 11/2002 | Shin et al. | .................. 73/54.07 |
| 6,715,139 | B1 * | 3/2004 | Kodosky et al. | ............ 717/125 |
| 6,802,053 | B1 * | 10/2004 | Dye et al. | .................... 717/113 |
| 6,873,928 | B2 * | 3/2005 | Thurman et al. | ............ 702/127 |
| 7,219,306 | B2 * | 5/2007 | Kodosky et al. | ............ 715/763 |
| 2002/0196283 | A1 | 12/2002 | Petruk et al. | |
| 2003/0035004 | A1 | 2/2003 | Dove et al. | |

FOREIGN PATENT DOCUMENTS

WO      WO-02/42987       5/2002

OTHER PUBLICATIONS

A. Franck "Integration of the Rheometer into Today's Formulation Laboratories" American Laboraty, pp. 29-30, Jun. 2002.

* cited by examiner

*Primary Examiner*—Tadeese Hailu
(74) *Attorney, Agent, or Firm*—Aslan Baghdadi; Paul, Hastings, Janofsky & Walker LLP

(57) ABSTRACT

System and methods are described for dynamically controlling operation of a rheometer. A program is created on a programming interface for executing a test upon a sample in a rheometer by receiving user selections of a plurality of nodes and connections of each node to another node according to directional connection indicators. Nodes indicate steps for performing a test upon a sample or configuring a rheometer for performing a test upon a sample. Scripts are created for generating a sequence of instructions to the rheometer. The scripts include instructions for performing steps indicated by each of the selected nodes and in accordance with the directional connection indicators. Low-level instructions are downloaded from the scripts for execution in the rheometer, and drivers in the rheometer are instructed for performing the downloaded instructions.

28 Claims, 11 Drawing Sheets

VMB Flow

SYSTEM AND METHOD FOR DYNAMICALLY CONTROLLING OPERATION OF RHEOMETRIC INSTRUMENTS

This application claims the benefit of U.S. Provisional Application No. 60/454,346, filed Mar. 14, 2003, which is herein incorporated by reference in its entirety.

BACKGROUND OF THE INVENTION

1. Field of the Invention

The present invention relates to operation of rheometric instruments, and more particularly, to graphical and programming interface systems and methods for dynamically controlling operation of rheometric instruments.

2. Background Information

The term "rheology" relates to the study of the deformation and flow of matter. Rheological testing was originally associated with the examination of properties and behavior of materials such as asphalt, lubricants, paints, plastics, rubber, and fluids. Such materials may exhibit rheological properties that are not easily described through classical fluid mechanics and elasticity. Developers of other products, including many that are associated with general consumer use, are also studying the rheological aspects and profiles of their respective products, because the changes to a product's consistency in response to applied conditions (e.g., vibration or stress) may affect its performance. Such products include plastics (bottles, films), food condiments (e.g., chocolate, mustard, ketchup, or salad dressings), cosmetics (e.g., nail polish, hair products, creams and lotions), and toiletries (e.g., toothpaste, deodorants).

Rheological instruments, or "rheometers" (also referred to as viscosimeters or viscometers), can be used to measure intrinsic material characteristics relating to, for example, a substance's viscosity or modulus. Viscosity is an internal property of a fluid that offers resistance to flow (i.e., it concerns the thickness of a liquid). Rheological measurements can be performed by, for example, placing a sample between parallel plates, and performing a variety of tests, such as controlled stress tests, controlled strain tests, dynamic mechanical tests, etc.

Known rheometers are typically designed to enable a user to perform a test selected from a discrete number of different available test procedures that are implemented in the instrument firmware, and executed by a dedicated CPU in the instrument hardware. A user operates the instrument by means of a graphical user interface program typically hosted on a PC connected to the rheometer via a serial port or network connection. Once a type of test is selected, the user interface may provide a form or template, and the user is instructed to enter a set of parameters and possibly certain options that are associated with the test to complete the form. Some rheometers enable users to configure the instrument to perform a sequence these tests, allowing uses to separately configure the parameters in each test.

For example, a user of a rheometer or other operator may be interested in testing the viscosity of asphalt using a frequency sweep test. A sinusoidal strain signal is applied to the asphalt at a fixed amplitude and range of frequencies selected by the user, and the resulting stress signal is measured, with data points reported at each frequency to determine trends in viscosity as the frequency is changed. For other measurements, for example, an amplitude sweep and a temperature sweep can be performed.

Modern rheometers are pre-configured, or pre-programmed, to perform types of tests that are typically performed on certain substances. For example, known instruments are configured to perform between ten and thirty different types of pre-programmed tests, where parameters for each test procedure are adjustable according to different frequency, amplitude, temperature, etc. profiles. Like most electronic devices, an advantage associated with operating a pre-programmed system is that any of the available tests can be easily configured in a simple-to-use graphical user interface. In this manner, a rheologist need not consult with a computer programmer in connection with frequently-performed tests and experiments.

As the field of rheology continues to evolve, it is becoming more common for scientists to customize testing of materials in a manner that was not anticipated by instrument manufacturers. For example, it would be unlikely that conventional rheometers are pre-configured to run a temperature ramp concurrently with frequency sweeps. In conventional rheometer systems in which the testing procedure is completely integrated with the instrument, it might not be possible to alter the instrument programming to achieve this level of customization without modifications to the instrument firmware and the controlling software. If the controller for the interface is PC-based, then the instrument owner may be able to retrofit the software to perform the specialized test, but only after significant computer programming is performed. Such alterations to the user interface may detract from performing other tests using the instrument, and the information required to make these modifications is generally not available to the end user. Accordingly, the pre-configurability of conventional rheometer instruments is disadvantageous in situations where a scientist wishes to design a customized testing pattern.

In view of the foregoing, it can be appreciated that a substantial need exists for a method and system for performing more flexible and customized testing of a sample on a rheometer. An improved interface is thus desired that is easy-to-use, but provides additional functionality for enabling users to design and execute customized testing in addition to more commonly-performed testing.

SUMMARY OF THE INVENTION

A method is described for dynamically controlling operation of a rheometer. A program is created on a programming interface for executing a test upon a sample in a rheometer by receiving user selections of a plurality of nodes and connections of each node to another node according to directional connection indicators. The nodes indicate steps for performing a test upon a sample, configuring a rheometer for performing a test upon a sample, or analyzing the data generated by such tests. Scripts are created for generating a sequence of instructions to the rheometer. The scripts include instructions for performing steps indicated by each of the selected nodes and in accordance with the directional connection indicators. Low-level instructions are downloaded from the scripts for execution in the rheometer, and drivers in the rheometer are instructed for performing the downloaded instructions.

A method is also described for dynamically creating test sequences for a rheometer. A plurality of nodes are selected, wherein nodes indicate steps for performing a test upon a sample or configuring a rheometer for performing a test upon a sample. Each node is connected to another node according to directional connection indicators. Parameter values that are associated with particular nodes are selected. When parameter values for a first node depend upon results of a second node, the first and second node are connected according to data flow indicators.

An additional method is described for dynamically configuring a rheometer to perform customized testing. A programming interface is provided for receiving user selections of a plurality of nodes and connections of each node to another node according to directional and data flow connection indicators. Nodes indicate steps for performing a test upon a sample or configuring a rheometer for performing a test upon a sample. Scripts are created for generating a sequence of instructions to the rheometer corresponding to programs created in the programming interface. Low-level instructions are downloaded from the scripts to the rheometer, wherein the rheometer is configured to execute low level instructions in a program sequence engine for operating drivers in the rheometer.

A system is described for dynamically controlling operation of a rheometer. The system includes a programming interface for executing a test upon a sample in a rheometer by receiving user selections of a plurality of nodes and connections of each node to another node according to directional connection indicators. Nodes indicate steps for performing a test upon a sample or configuring a rheometer for performing a test upon a sample. A scripts generator generates a sequence of instructions to the rheometer, wherein the scripts include instructions for performing steps indicated by each of the selected nodes and in accordance with the directional connection indicators. An output interface downloads script files to a program sequence engine in a rheometer for executing low-level instructions for operating drivers in the rheometer.

The present invention relates to a method and system for creating tests to be performed on a rheometer instrument using a robust, programmable interface. The interface enables users to assemble pre-configured test procedures or to custom-build tests using a scripting programming language. Custom-built tests can be stored for later use or inclusion within other tests. Forms are dynamically generated according to the type of test that is created and the parameters associated with the test, and forms also can be customized to prompt users only for specified parameter values. The graphical user interface includes a drag-and-drop, icon-based visual system to facilitate easy programming and configuration, in addition to tree views illustrating the hierarchical nature of test design and preparation.

DETAILED DESCRIPTION OF THE INVENTION

Overview

The system and method described herein provide a new approach for creating tests in a rheometric instrument by removing automated, "packaged" functionality from the rheometer instrument itself and utilizing instead a robust graphical user interface that enables users to custom-build test procedures as an alternative to (or in addition to) selecting conventional "pre-built" testing mechanisms. The interface is based upon use of Instrument Sequence Language (ISL), which provides an environment containing generic programming logic constructs (FOR/WHILE loops, GOTOs, GOSUBs, etc.), polymorphic memory registers, specialized instrument instructions for operations such as motor and environmental control, and data acquisition, and special instructions for the synchronization of those operations.

With this system and method for operating a rheometer, users can utilize drag-and-drop icons in a graphical user interface for creating pre-defined tests, or can build complex test methods by wiring together predefined blocks of code and simple logic flow elements. The graphical programming environment also allows advanced users who require customization to develop robust testing protocols by exposing the low-level functionality of the instrument hardware. Standard script controls and languages, such as JavaScript® and HTML, can also be used for programming instead of instrument-specific proprietary tools, and the instrumentation software can be integrated with other Windows® applications via standard automation interfaces. The scripting system can also integrate data storage, presentation, and analysis components.

As an exemplary embodiment of the present invention, a user interface is described for controlling operation of a rheometer instrument and a separate data analysis and presentation tool that is connected to the outputs of the rheometer. It is to be understood, however, that the present invention is not limited to a particular three-unit configuration. The invention is equally applicable, for example, to a two-unit rheometric system comprised of an instrument and a controller or a system wherein the instrument, the analysis and presentation tools, and the user interface are integrated within a single unit and also to systems in which the components are distributed over more than three units.

System Components

Figure 1:
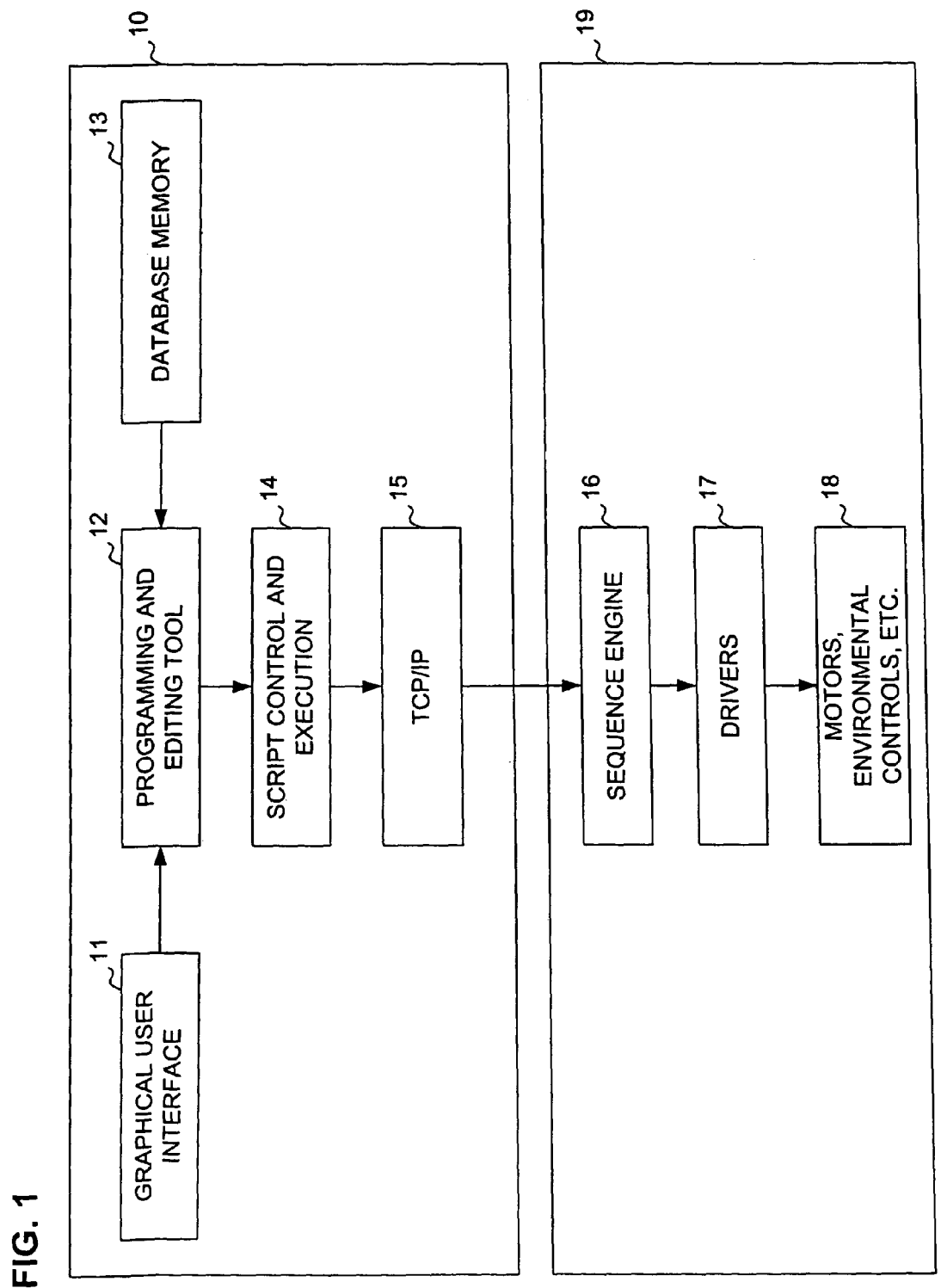
FIG. 1 is a schematic diagram illustrating connections between an instrument interface and an instrument according to an embodiment of the present invention.

In accordance with an embodiment of the present invention, an instrument interface is provided for remotely controlling operation of an instrument. As shown in FIG. 1, an instrument interface 10 connects to an instrument 19 via a TCP/IP connection 15 (or any type of networked connection). The instrument 19 is configured to receive TCP/IP communications in the form of binary Instrument Sequence Language (ISL) instructions, and these instructions are input to a sequence engine 16 for execution. The sequence engine is a type of "virtual machine" implemented in code in the instrument CPU that consists of a state machine with a set of instructions that can be executed, and a series of memory addresses that can be used to store data in a variety of different formats. Execution of the scripts provides low-level, step-by-step instructions for hardware drivers 17, which transmit commands for operating motors, environmental controls, etc. 18, provided within the instrument.

The ISL consists of several types of instructions. The first type of instructions are general purpose programming operations that are used to control program flow, such as GOTO, IF, FOR, SWITCH, etc. Instructions are also provided for accessing instrument memory within the ISE virtual machine, for general arithmetic operations (addition, subtraction, multiplication, division, modulo), and mathematical functions such as trigonometric functions, logarithms, etc. Special purpose instructions specific to rheological testing are also defined in the ISL. These instructions are used to control various hardware systems in the rheometer and include motor control instructions (for defining the stress or strain profile to apply to the sample being tested), instrument stage control instructions (for control of the sample stage during sample loading operations or during tests), environment control instructions (for controlling sample temperature profile and switching between the various environmental hardware options), and instructions for controlling the timing of instruction execution (many operations carried out by the instrument are either time-critical, or depend upon previous instructions already having been completed, and these instructions allow ISL scripts to control how and when they are executed).

ISL statements are fixed-length binary structures that consist of an instruction header and a content field. The format of the instruction header is common to all instructions, consisting of a sequence number, an opcode that defines the instruction type, a check sum, a version identifier, and a field of special purpose bits that can be used for various applications such as debugging. The format of the content field is specific to each instruction, and contains the various operands to the instruction.

A compiler is provided for translating ISL source code into binary ISL instructions. This compiler can be used as either a command line tool for compiling source files into binary ISL library files for use in the VMB, or as a combination editor/compiler that allows authors to create new ISL scripts, flag syntax errors, and provide online help on the format of specific ISL instructions.

The ISL scripts are generated dynamically in the instrument interface 10 via a programming and editing tool 12 which builds the scripts from information contained in the high level node objects. The tool may be connected to a graphical user interface 11 that enables users to graphically program tests for the instrument by creating and editing node based scripts. This graphical user interface may be icon-based, and may utilize flow charts, trees, or other mechanisms by which users can specify tests and values for test parameters for performance in the instrument. Forms, field definitions, pre-constructed tests objects, and test options are stored in databases 13 for use in building tests in the programming tool 12.

Once a test method is programmed by a user, scripts are dynamically generated in a script control 14 component, which generally includes instructions associated with performance of a test programmed by the user. This script contains instructions to be executed within the script control 14, and may also contain sections of ISL code that are sent to the instrument and executed during the course of the method execution. These ISL scripts are received in a TCP/IP interface for transmission to the instrument.

Using the system as described with reference to FIG. 1 for programming and operating an instrument, the primary, high-level functionality associated with designing and constructing a test sequence is located in the instrument interface 10, as opposed to in the instrument itself. However, the scripts that are to be executed for instructing hardware drivers to operate the motors, data acquisition systems, environmental controls, or other such devices that are associated with the instrument, are executed in the sequence engine 16 of the instrument. In this manner, the instrument interface, which may operate on a laptop or PC, need not be a dedicated machine for operating the instrument. Particularly, once the ISL script that is sent over the TCP/IP connection is downloaded to the instrument, the instrument can operate without further intervention from the interface. Therefore, the laptop or PC can then be used for operating other instruments, or other laptops or PC's can be easily connected (for example, via a network connection) for downloading scripts for subsequent experiments. Additionally, the PC used to build and download the ISL script to the instrument does not need to be in close physical proximity to the instrument.

Figure 2:
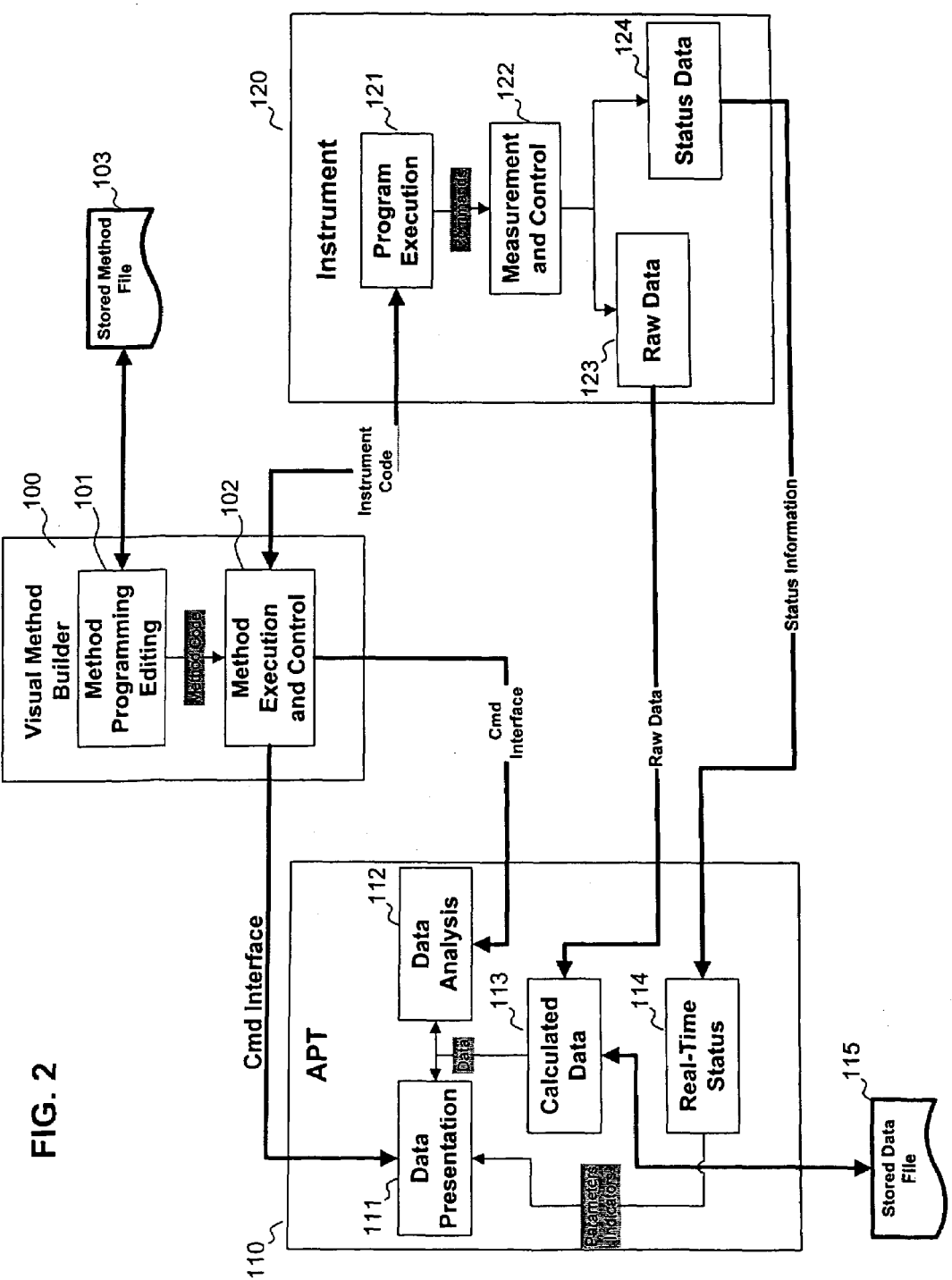
FIG. 2 is a schematic diagram that illustrates connections between main system components in an exemplary embodiment of the present invention.

FIG. 2 is a schematic diagram that illustrates connections between main system components in an exemplary embodiment of the present invention. As can be seen, the system includes a "visual method builder" ("VMB") component 100, an "analysis and presentation tool" ("APT") component 110, and an "instrument" component 120.

Known rheometer systems include APT and instrument components, but the configuration and capabilities of these components must be modified to be compatible with the VMB component in accordance with an embodiment of the present invention. In known systems, a user interacts with the APT component to make selections from a list of pre-configured tests and specify appropriate test parameters in a form. The APT component then transfers these parameters and "commands" the instrument to begin making measurements and acquiring data, and to relay completed measurement information back to the APT. Upon receiving a "start" signal from the APT, the instrument performs each step of a pre-configured test as it is stored in the instrument memory. One or more processors and memory in the instrument itself are utilized for receiving a test command (e.g., start test #9) and for performing each of the steps of the pre-configured test. However, if a user wants to perform a test that is not pre-configured (e.g., a combination of test #9 and test #3), then the code within the instrument must be changed, but the instrument is not designed to be reprogrammed at the consumer level.

As can be seen in FIG. 2, the Visual Method Builder component 100 includes a "Method Programming and Editing" section 101 and a "Method Execution and Control" section 102. A "method" is a flow chart that represents a collection of nodes that can be executed (such as test blocks, script blocks, or analysis code). The method defines what is executed and the logic in order to determine the order in which the execution steps should occur. As described below, hierarchical arrangements are possible, where methods are nested within other methods.

Section 101 represents the graphical user interface, scripting tools, and any other means by which a user selects, designs, or reconfigures a method for performance. Since the interface includes the pre-configured functionality that is provided in conventional systems, and since users will want to save their custom-programmed methods for subsequent testing, this section is in communication with memory storage 103 to store and retrieve memory files. "Method Execution and Control" section 102 provides the instructions for the instrument to perform the test or tests provided in the method, and to the APT to perform any data analysis and data presentation steps. The instrument instructions are converted into Instrument Sequence Language as needed during the script execution and provided to the instrument 120, and commands are sent to the APT 110 for organizing data presentation and analysis as required the user.

The instrument component 120 in FIG. 2 includes a "Program Execution" section 121, a "Measurement and Control" section 122, a "Raw Data" section 123, and a "Status Data" section 124. The "Program Execution" section receives the instrument codes from the "Method Execution and Control" section 102, and executes the codes, sending commands to "Measurement and Control" section 122 to measure strain, temperature, etc., according to instructions from the VMB component. Finally, measurements and status information is provided to the APT component from "Raw Data" section 123 and "Status Data" section 124, from which the APT component can perform calculations and provide reports.

As the third component 110, the APT receives instructions from the VMB 100 to generate reports to the user in "Data Presentation" section 111 or to perform analysis in "Data Analysis" section 112 based upon the raw data received from the instrument. The raw data is converted to rheological parameters in "Calculated Data" section 113, and is presented to the user in either a graphical or tabular form. "Real-Time Status" section 114, receives information from the instrument concerning the current state of instrument systems (environmental conditions, data acquisition states, etc). The calculated data can be stored in a data file 115 for subsequent tests and analysis.

Visual Method Builder Subsystems

Figure 3:
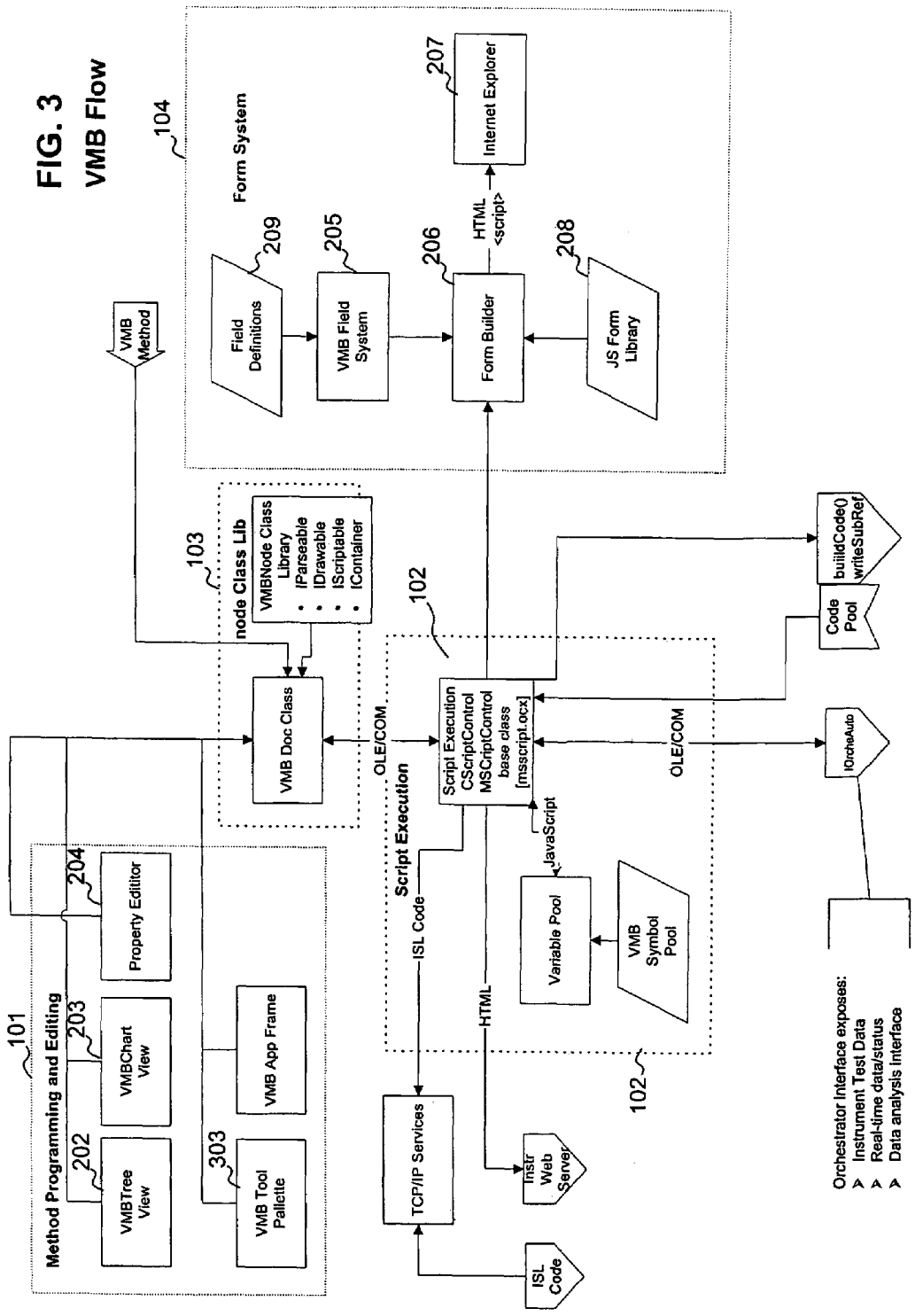
FIG. 3 is a schematic diagram of subsystems within each of the four sections of the VMB component of FIG. 2, in accordance with an embodiment of the present invention.

Describing the Visual Method Builder (VMB) component 100 in further detail, the Method Programming and Editing section 101 and Method Execution and Control section 102 are additionally supported by a "Node Class Library" and a "Form System," as shown in FIG. 3.

As introduced above, the Method Programming and Editing section 101 contains tools for creating, editing, and manipulating VMB "nodes" and "properties." A "node" is a single object in a VMB method, which can represent a test block, a script block, analysis code, or an entire method. A "property" represents a name/value pair that gives the value of some parameter. The Method Editing system includes several different views for enabling users to build a method and perform edits.

A "Node Class Library" 103 defines the behavior of "nodes," the links between nodes (these are later defined as "wires"), and names/values for parameters for performing a test (or "properties"). The Node Class Library itself is transparent to the user, such that users do not interact with the library itself, but is used to define the rules for editing and constructing method and the interaction between nodes. The Method Programming and Editing section 101 of the user interface interacts with this library.

A "Form System" 104 is used for generating forms based upon content in the VMB nodes and information stored in a field database system. The Form System can also be used to display forms to query users for parameter values, either on the PC on the instrument display via an embedded web browser.

Finally, the "Method Execution and Control" section 102 is a script execution system for executing the code that is generated by the VMB nodes, and coordinating execution of that code with code downloaded and executed in the instrument Program Execution section 121.

FIG. 3 provides a schematic diagram of the subsystems within each of the four sections of the VMB component 100, which will now be described in turn.

Method Programming and Editing Section

The method editor comprises a number of subsystems that are used to view and edit VMB methods. FIG. 3 illustrates several different visual representations of methods that may be provided, including: a VMBChart subsystem 201 that presents the method in the form of a flow chart, a VMBTree subsystem 202 that provides a Tree View of the method, a VMBPalette 203 that contains previously-defined resources (stored tests, geometries, analysis blocks etc.), and a property editor 204 that allows individual properties in nodes to be manipulated. These components are contained within a single software application framework (VMB App Frame) what facilitates interaction between these systems.

Figure 4:
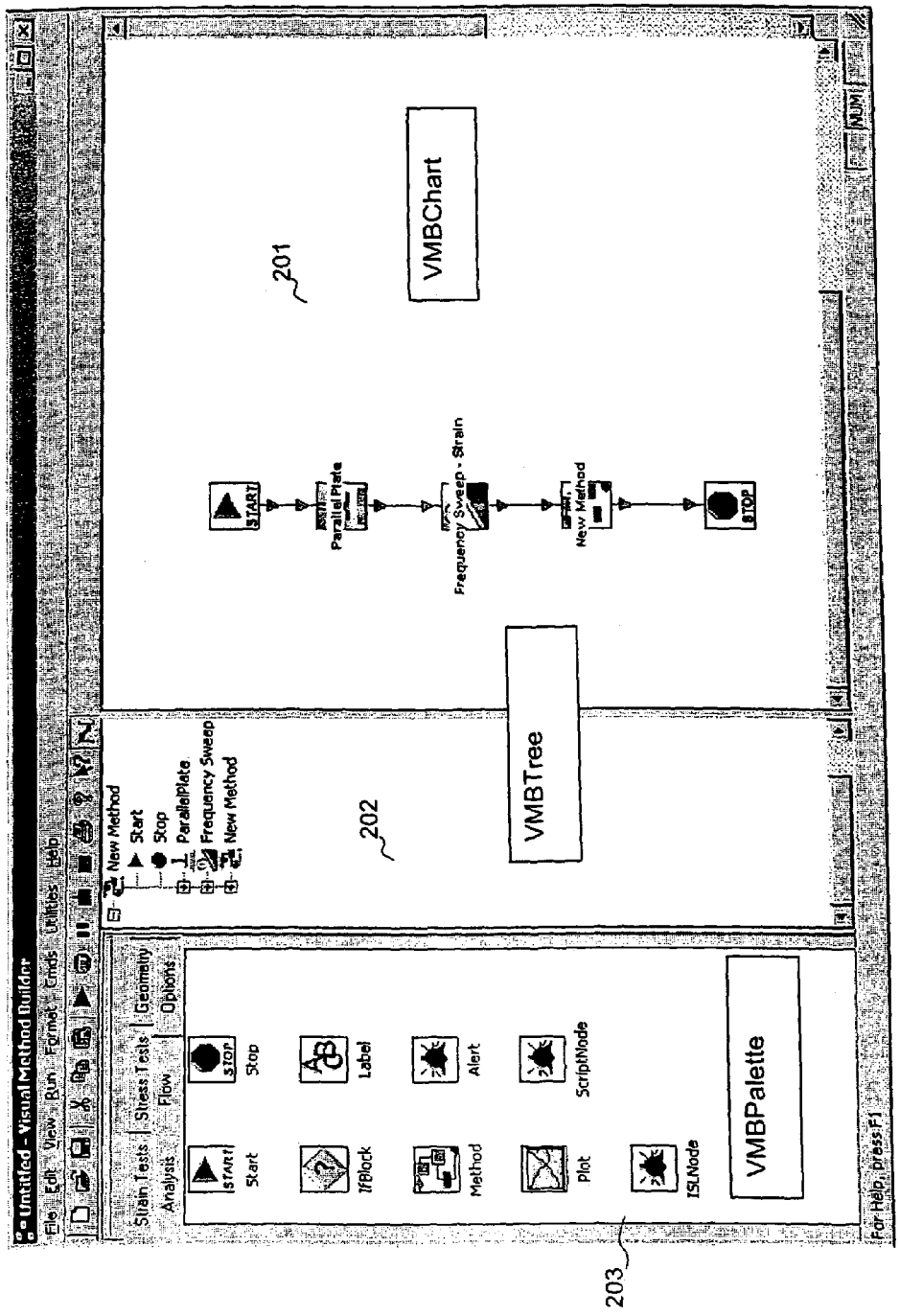
FIG. 4 is an exemplary visual representation of the Method Programming and Editing section of the VMB component of FIG. 3 on a graphical user interface, in accordance with an embodiment of the present invention.

FIG. 4 provides an example of a visual representation of the Method Programming and Editing section 101 of the VMB component 100 on a graphical user interface, illustrating VMB Chart 201, VMB Tree 202, and VMB Palette 203. These subsystems are contained in a single window, and are separated by splitter bars that can be adjusted by users. Additionally, each component can be toggled on and off, and floated outside of the frame or docked in it. Each of the editing components in the VMB Method Editor can be used to modify the underlying VMB method. Making a change in one editor automatically causes the view presented in the other editor to update to reflect the changes made to the method. This includes changes in the selected node in each editor component.

Additional detail with regard to each of these subsystems will now be described.

VMB Chart

The VMBChart 201 renders the current method in the form of a flow chart, allowing users to manipulate VMB nodes graphically by selecting and dragging components via a keyboard and mouse. The flow chart also provides visual information regarding an order in which nodes are executed when the method is run.

The flow chart editor (VMBChart) is used to display the currently-active method, showing its nodes and wires in their current positions in the flow chart. Since methods can be nested (as will be further described in greater detail below), the VMBChart provides mechanisms for zooming in (expanding child nodes), or zooming out (collapsing to the node parent). The VMBChart also provides a mechanism for indicating what node is the selected node.

A drag-and-drop interface is provided to allow nodes to be added to methods from the library of stored methods found in the VMBPalette. Nodes can also be added to the active method by copying and pasting using the windows clipboard.

The properties contained within a node can be edited by double-clicking on the node to invoke the appropriate editor (e.g. the property editor for nodes containing properties, a script edit form for script nodes). Additional editing functions can be accessed by right clicking to display the node context menu, which lists the relevant operations. Functions can also be accessed in the VMB menu bar or toolbar.

Figure 5:
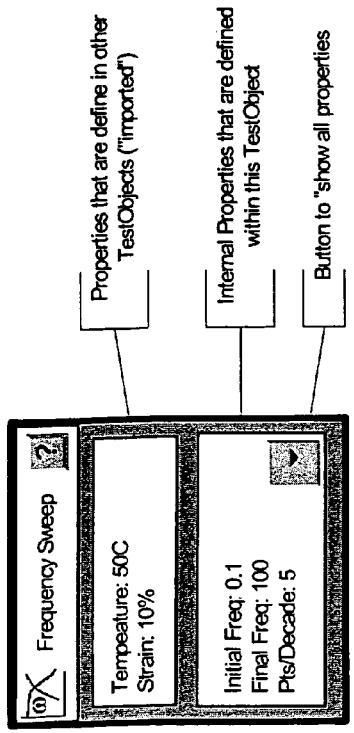
FIG. 5 is an exemplary visual representation of a property summary view within the Method Programming and Editing Section of FIG. 3, in accordance with an embodiment of the present invention.

Finally, nodes can be visually presented in one of two formats, an icon format as shown in FIG. 4, or a "property summary view," as shown in FIG. 5. The property summary view provides a summary of the properties that are imported and exported by the node.

The vertical lines that connect one node to another are known as "wires." A "flow wire" is a directional connection, indicating the order in which the operations should be executed. Each node includes "flow plugs" by which one or more wires can be connected. If performance of a node is dependent upon properties that are resolved in accordance with execution of another node, the node also may include one or more "data plugs," which are connected by "data wires" to other nodes. These data wires are used to feed the information forward to the node requesting the information.

VMB Tree

Figure 6:
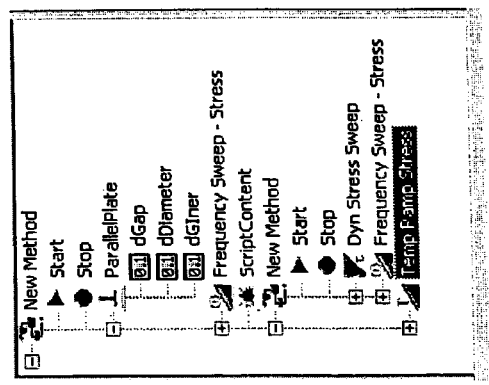
FIG. 6 is an exemplary graphical user interface illustration of a tree of a method constructed in the Method Programming and Editing Section of FIG. 4, in accordance with an embodiment of the present invention.

The VMBTree 202 or Method Navigator provides an expandable hierarchical "Tree View" of the current Method, representing each of the flow chart objects, and object "properties" as separate nodes. These nodes can be either expanded or collapsed to display or hide content as desired. This provides a quick way of navigating through all of the elements in a method, and provides information about properties in the elements. An expanded view of a graphical user interface containing a tree is provided in FIG. 6.

This control functions as a standard Windows Tree View control, presenting nodes that can be expanded or collapsed depending on whether the node has child nodes which are contained within it. Each node contains a text description, a small icon depicting the type of the node, and an optional description text, which is displayed as a tooltip. In this view the VMB nodes are displayed, however wires between those nodes are not displayed in the Tree View list. Unlike the VMBChart, the VMBTree allows node content located in different levels to be viewed and manipulated without having to zoom-in and zoom-out between the different methods.

VMB Palette

The VMB Palette subsystem is used for adding new nodes (tests, geometries, scripts, etc.) to a currently active method. A drag-and-drop interface is used to add the nodes to the active method in the VMB Chart or VMB Tree. As shown in FIG. 4, nodes in the VMB Chart 201, such as "Start" and "Stop," are found in the VMB Palette 203. As another example, the icon for "Parallel Plate" that is shown in the VMB chart would be found in the VMB Palette 203 under the subcategory "Geometry." Each icon in the palette is known as a "widget," which represents storage of node information that can be accessed from a library for use in building a method.

Figure 7:
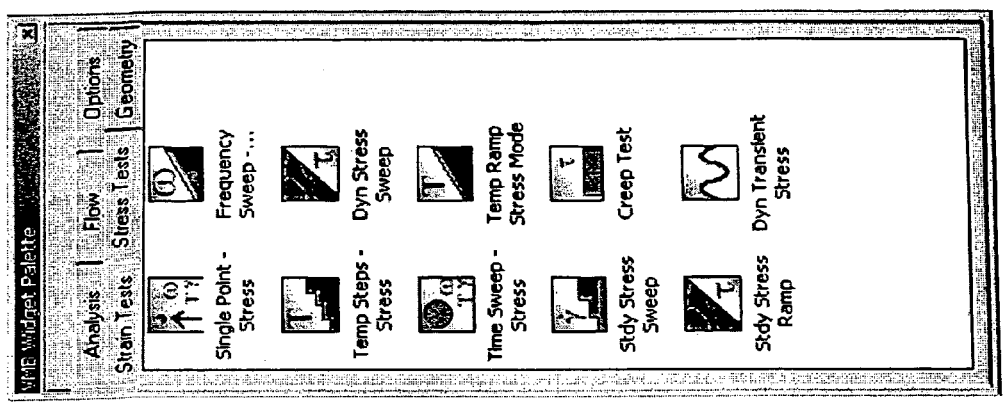
FIGS. 7 and 8 are exemplary graphical user interfaces illustrations of a VMB Palette provided to a user in the Method Programming and Editing Section of FIG. 4, in accordance with an embodiment of the present invention.
Figure 8:
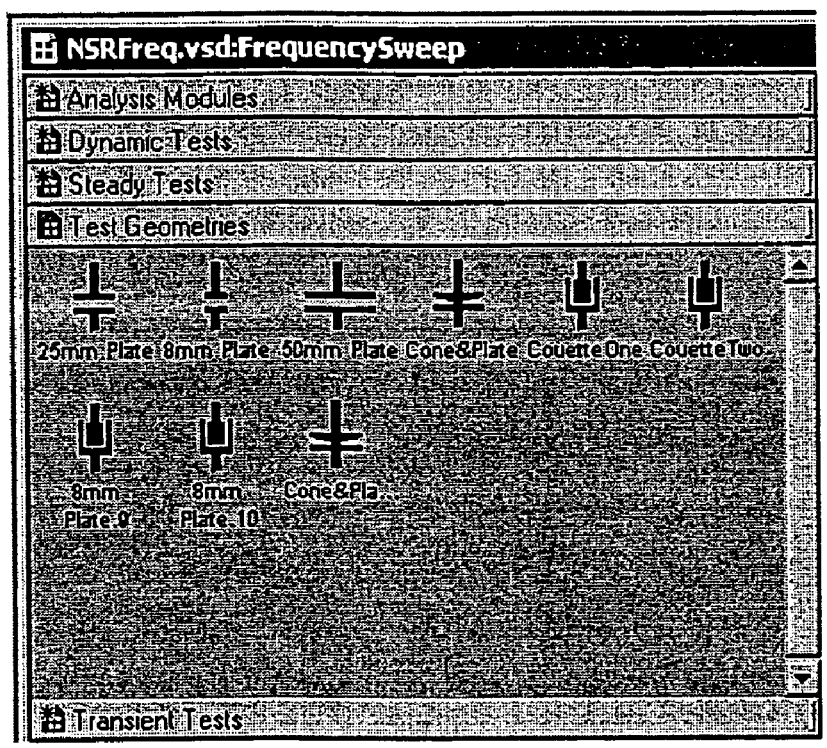

FIG. 7 illustrates a VMB Palette 203 in which the subcategory "Stress Tests" is highlighted. Other subcategories shown in FIG. 7 include "Analysis," "Flow," "Options," "Strain Tests," and "Geometry." The "Analysis" subcategory represents different data analysis functions that may be invoked in a VMB method. The "Flow" subcategory is comprised of nodes that control the flow of the method, such as such as "START," and "STOP" nodes, and logic nodes such as "IF" or "FOR". The "Geometry" subcategory may be organized to represent different sample test geometry types (e.g., parallel plate versus cone and plate), or it may be organized to represent physical tools that a customer may own (e.g., 25 mm plates versus 50 mm plates).

The VMB Palette can be organized in several different ways, but should preferably be presented in a manner that is intuitive to a user for selecting nodes to build a method. As other examples, a "Predefined Tests" category could include "Controlled Stress Tests," "Controlled Strain Tests," "Steady Tests" and "Dynamic Tests." A "Stored Methods" subcategory could include all of the VMB methods that have been built by a user or contained in a user-defined directory. Since the interface is a hierarchical system, a "node" may be an entire "method," or a collection of nodes.

VMB Property Editor

Referring back to the "Method Programming and Edits" section 101 of the VMB component in FIG. 3, another subsystem is the VMB Property Editor 204. The VMB Property editor is utilized for editing VMB property nodes. As defined above, "properties" are named parameters that have values. These parameters values can be in the form of floating point values, integer values, or character strings, and can be either single values, or an array of values. The Property editor is used by a user to view and edit the collection of property values within a node, and can also be used to add or remove additional properties. The Property Editor is designed for advanced users, who wish to construct new tests, change the way that predefined tests operate, or change the default parameter values in a test. It is not designed to be a normal way to change test parameters. The preferred way to do this is by using the "Form System" section 104, as will be described below.

In other words, in the normal course of operation, when an icon is selected in the VMB Palette, such as "Frequency Sweep" shown in the upper right corner of FIG. 7, a "Frequency Sweep Form" template is generated and displayed, which prompts the user to provide values for a series of different parameters that are associated with performing a frequency sweep (e.g., start frequency, end frequency, increment value, time between increment values, etc.). The VMB Property Editor 204 is used to allow a user to control which parameters are to be presented in the form, to have greater control over operation of that node in the method.

Figure 9:
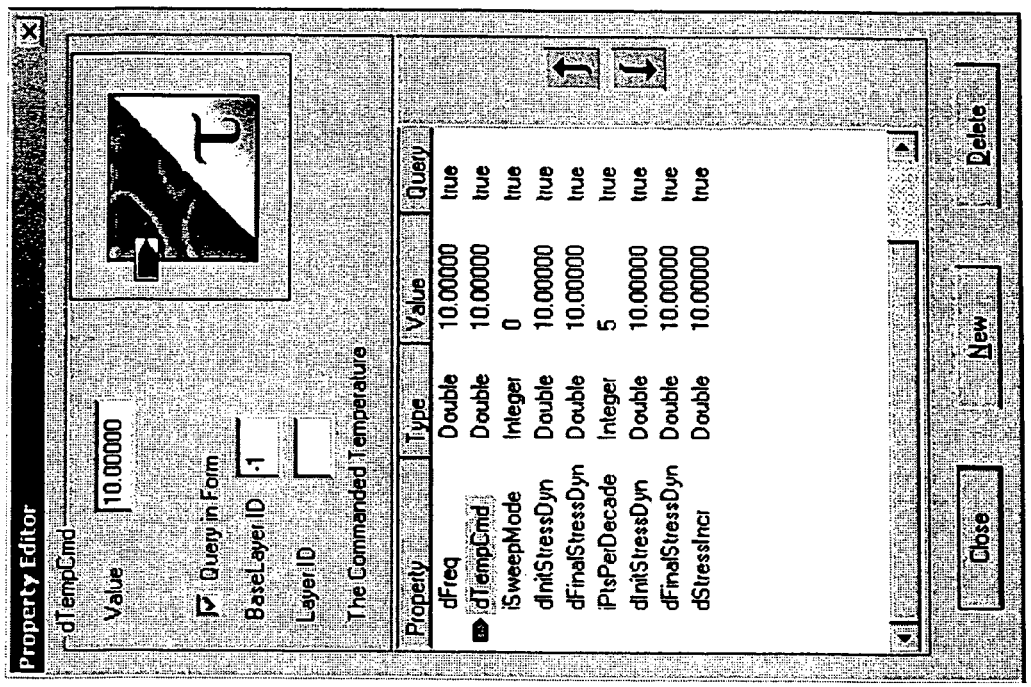
FIG. 9 is an exemplary graphical user interface illustration of a view of the VMB Property Editor subsystem of FIG. 3, in accordance with an embodiment of the present invention.

FIG. 9 is an exemplary screen shot of a view of the VMB Property Editor subsystem, which includes a chart containing a list of properties, and each property is associated with a "type," a "value," and a "query." The "query" column of the chart indicates whether the parameter is to use only a default value, or whether it is to be included in forms generated by the for system component, allowing general users to change its value.

VMB Form System Section

Referring back to FIG. 3 again, on the right side of the figure is a VMB Form System section 104. As described above with reference to conventional, pre-configured rheometer systems, once a test procedure is selected, the system provides one or more forms containing a template with parameters. The user is prompted to complete the form by entering parameter values associated with the selected test. In contrast with such a conventional rheometer system, the VMB Form System section 104 can be used for dynamically creating HTML-based forms that allow users to change the values of VMB properties (e.g. test parameters) using a familiar "test setup" interface. The form system also contains features for displaying and enforcing limits (i.e. maximum and minimum allowed values) for a given field based on values calculated from other properties.

Figure 10:
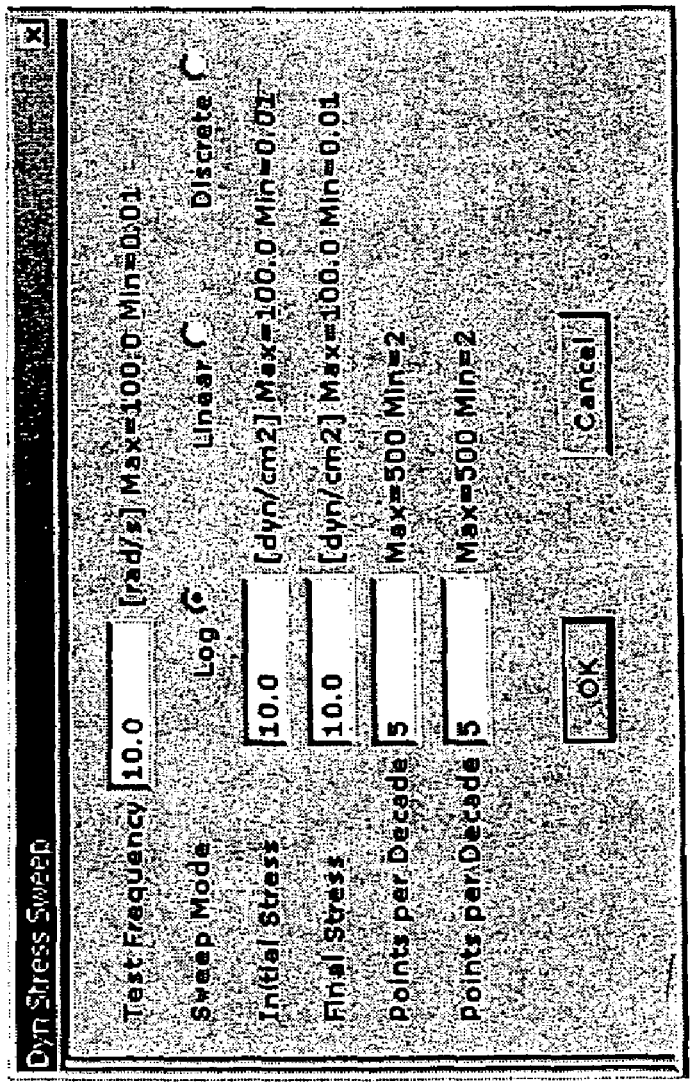
FIG. 10 is an exemplary graphical user interface illustration of a view of a form that is generated to prompt a user to enter parameter values relating to a Dynamic Stress Sweep test, in accordance with an embodiment of the present invention.

FIG. 10 is a screen shot providing a view of a form that is generated for a Dynamic Stress Sweep. As can be seen, the generated form prompts the user to provide a "test frequency," an "initial stress" value, a "final stress" value, and "points per decade."

Forms are typically used for VMB nodes such as test nodes that contain test parameter information in the form of VMB properties. Each property in the test node corresponds to a given field in the form, with the text and formatting information for the field being defined in a field database system. Note that it is possible to selectively hide fields, so that all properties may not be displayed in the form. The order of the fields in the form is determined by the order of the properties in the node. Sets of fields may be dynamically shown or hidden while the form is displayed by using different HTML layers, as defined by attributes in the properties.

The form system consists of several components that are used to create new HTML forms based on VMB node content, display these dynamic forms (or any HTML content), handle user interaction with the form, and provide mechanisms for things such as range checking and field validation. The form system is composed of four main elements, as shown in FIG. 3.

The VMB Field System 205 is used to define how each VMB Property is rendered as a field. This system is used in conjunction with a field definition file 209, which contains the actual format of the field (using a combination of HTML and XML tags). The field definition files each include a field name, or field ID a field type (e.g., text versus checkbox) and format (e.g., integer versus decimal).

The JSForm Library 208 is a library of functions written in JavaScript that are used with the forms generated by the VMB Form System. This library includes functions for field formatting, range validation, and control of the different layers used in these forms.

The Form Builder 206 is used to take information found in VMB nodes and the VMB Field System and generate an actual HTML form. It is also responsible for extracting the changed field values from each node after the form has been edited, and making the appropriate changes in the VMB node.

Finally, the Web Browser Component 207 is a control with an embedded Web Browser component that handles actual rendering and control of the HTML form.

VMB Node Class Library Section

As can be seen in FIG. 3, user information created through the user interface in the Method Programming and Edits section 101 is fed into the VMB Node Class Library section 103.

The Node Class Library 103 is used to define the "behavior" of the VMB nodes, wires, and properties within a method. The library is not utilized directly by the user; it is the database that organizes the information provided by the Method Programming and Editor section 101 and retrieves necessary information to enable execution of the requested method.

VMB nodes contain information on how the nodes are rendered in the VMBChart (graphic bitmap used, size and position of the node, label for the node, etc.). Nodes also can contain plugs, which indicate how the nodes can be connected to other nodes via "flow wire" or "data wires." A flow wire connects two nodes indicating the direction of program flow (with a "source node" and a "destination node"). A data wire connects two nodes and provides a mechanism to propagate parameter values between the two nodes to allow information to be fed into a script.

VMB nodes are usually arranged in a hierarchical fashion, with "child" nodes contained by "parent" nodes, up to an arbitrary number of levels deep, as shown in the chart provided below of different node types:

| Node Type | Information content |
| --- | --- |
| VarNode | Property information - the name and value for a single property. |
| Method Node | A list of child nodes |
| Test Node | Sets of properties (as child nodes) and an index into the ISE code pool listing the chunk of code to execute during a test. |
| Script Node | A node that contains script content. This can be in ISL or JavaScript format. |
| Logic Node | A node that contains a logic block that details which flow wire to pass program flow to. |

The VMB Node class library implements four different interfaces that define the set of functions that are used within each node class. These interfaces are listed in the table below:

| Interface | Definition |
| --- | --- |
| IParseable | Defines functions needed to load/save basic class attributes from XML source elements. Defines other base class functionality. |
| IDrawable | Set of functions needed to render node graphically. Image index, node position, node, size etc. |
| IScriptable | Functions to allow node to be executed by Script control. Building code, executing code, containing code etc. |
| IContainer | Functions allowing node to contain child nodes, and to manipulate those nodes (add nodes, remove nodes, etc). |

The VMB Node class and all sub-classes are defined such that all node objects are guaranteed to implement the IParseable interface. Currently the classes are defined in such a way that objects implementing IContainer also implement IScriptable, IScriptable objects implement IDrawable, and IDrawable implements IParseable.

Script Execution Section

As shown in FIG. 3, the Script Execution section 102 executes scripts created by the VMB Node Class Library 103. These scripts are generally in the form of JavaScript (which is automatically generated by each node via methods in the IScriptable interface), but other scripting languages are also possible. The Script Execution section is also responsible for coordinating the execution of each script with the execution of ISE code in the Program Execution section 121 in the rheometer instrument 120, and with various functions in the APT 110 for performing data analysis 112 and presentation of results to the user 111.

Sequence Engine

The instrument sequence engine is used to control the operation of the various systems of the rheometer, including motor, stage, environmental control, and data acquisition. This engine executes ISL instructions that are typically sent to the instrument from the interface via a networked connection. The ISL instructions can be either in the form of scripts that have been downloaded into instruction tables or instruction commands that are sent for immediate execution.

EXAMPLE

Figure 11:
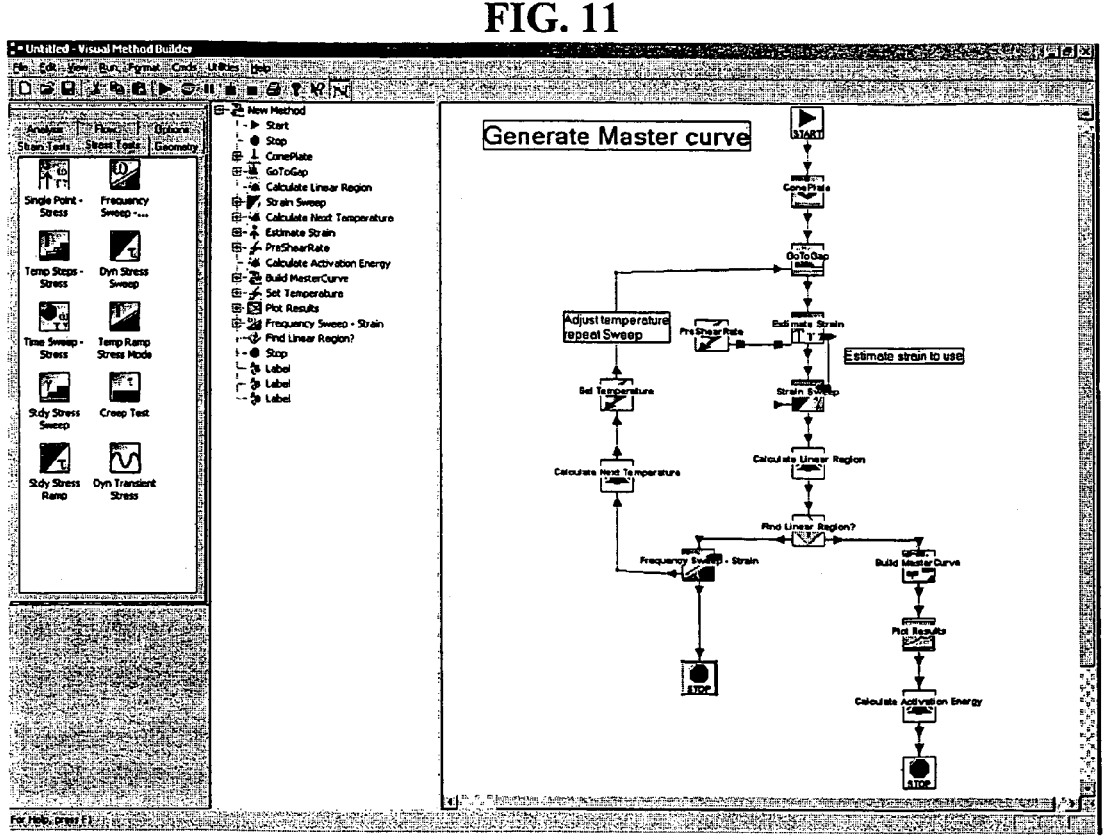
FIG. 11 is an exemplary graphical user interface illustration of a method constructed in a Method Programming and Editing Section, in accordance with an embodiment of the present invention.
Figure 12:
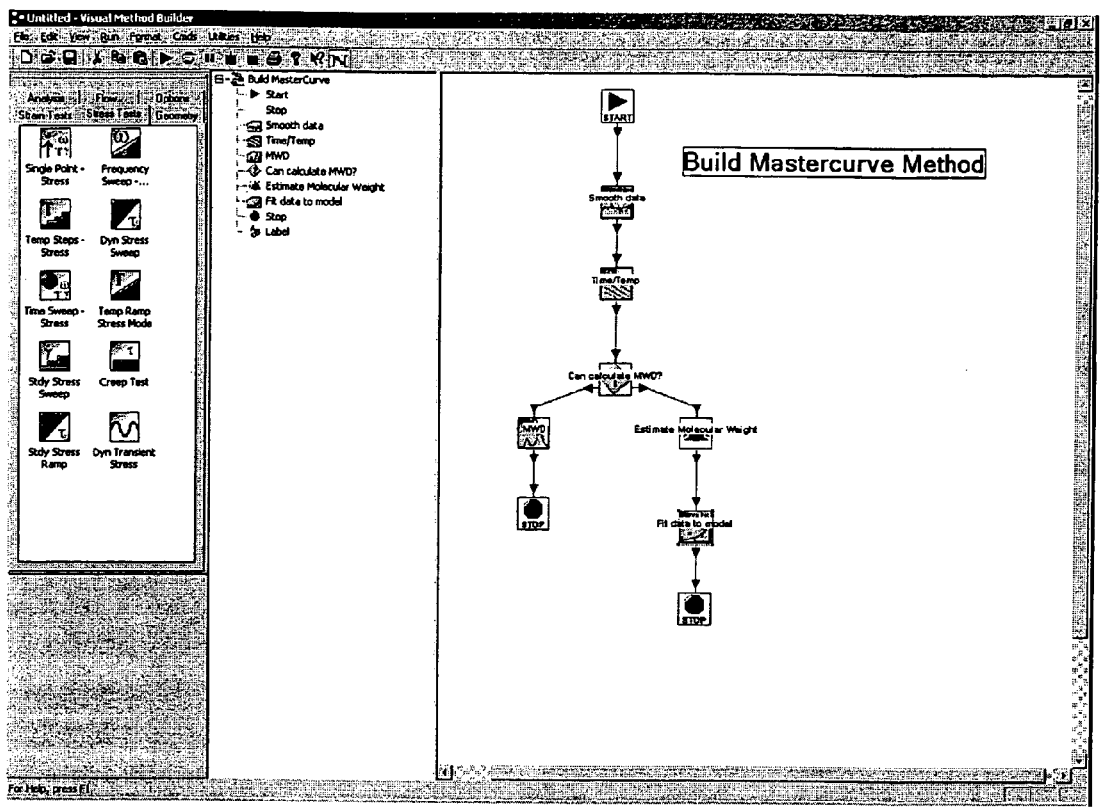
FIG. 12 is an exemplary graphical user interface illustration of a sub-method of the method of FIG. 11.

FIGS. 11 and 12 illustrate an example of a method that is generated in the instrument interface for operating an instrument. As can be seen in FIG. 11, the "Start" icon is automatically placed within the VMB chart to define a reference point for building a method. The next icon, denoted "Cone Plate," is selected from the "Geometry" category in the VMB Palette on the left, and is utilized for defining a test geometry. Particularly, the "Cone Plate" is related to the geometry of the sample. Once the "Cone Plate" icon is dragged-and-dropped into the chart, a "flow wire" is created between the two icons to indicate the directional flow to this node. By double-clicking on the "Cone Plate" icon, a form is displayed for the user to provide parameter values.

The chart next includes a "Go To Gap" icon, which relates to moving the platform, or stage, that holds the geometry to a predetermined position after a sample has been loaded. Thus, upon execution of a script in the instrument, the motors will receive signals to move to a certain position in accordance with the loading of the sample.

The next icon is labeled "Estimate Strain." The script that will be generated for this node instructs the instrument to run a single point measurement to get an initial value for the type of material being tested. As can be seen, this node is connected via flow wires to "Pre-Shear Rate" and "Strain Sweep," and is also connected to "Strain Sweep" via a data wire. The "Pre-Shear Rate" is another conditioning step, which is to be performed prior to the "Estimate Strain" process.

The results of the "Estimate Strain" node will be utilized for performing the "Strain Sweep." For this procedure, the instrument subjects the material to incremental deformations, deforming it to a greater degree and measuring parameters relating to the structure by its response.

The next icon is labeled "Calculate Linear Strain," which is a script node. The script looks at the data from the previous node and determines whether there is a sufficient linear range for performing a frequency sweep.

As can be seen, the method next includes an "IF BLOCK." If there is a sufficient linear range, a frequency sweep is performed (on the left), and if not, a "master curve" is constructed (on the right) from the previously measured data.

The "Frequency Sweep" icon is located to the left of the "Find Linear Region" IF BLOCK, and then continues in an upward direction through a loop. This illustrates the significance of direction flow wires, since flow chart can proceed in any indicated direction. Based upon data collected in the "Frequency Sweep," the system can determine whether to stop or run through another loop.

If another loop is required, another temperature value is calculated in the "Calculate Next Temperature" node, which is then submitted to "Set Temperature" for adjusting the temperature before repeating the sweep.

If there is not a sufficient linear range, the "Build Master Curve" node is executed. The node is a "parent node," encapsulating the method shown in FIG. 12. Particularly, as shown in FIG. 12, the system perform a "Smooth Data" operation to condition the data to remove random statistical noise, before performing "Time/Temperature Superposition." The system then determines whether a molecular weight distribution calculation can be performed. If this is not possible, it is estimated in the "Estimate Molecular Weight" node, otherwise a more rigorous calculation is made. Upon completion of the child nodes in the method, the system returns to the parent method of FIG. 11.

Thus, upon completing the step of "Build Master Curve," the system performs the "Plot Results," before "Calculate Activation Energy."

As can be seen, the instrument interface enables a user to graphically program an instrument using branching, looping, and encapsulation.

Functionality of the Interface

Use of the Visual Method Builder as described above in conjunction with a rheometer instrument enables significantly improved flexibility and functionality associated designing and conducting tests on a rheometer. Instead of being "pre-programmed" to run particular types of tests, the rheometer now receives detailed instructions, or "primitive operations" from the interface, which can be easily programmed without requiring additional software tools or retrofitting. This flexibility allows users to perform an almost infinite number of different tests, according to the specific needs of the scientist, and relating to the particular material or substance being evaluated.

As one advantage associated with this flexibility, the system and method enables users to download hundreds of different tests to the rheometer instrument all at once, so that the system does not require continuous user monitoring. This may be particularly useful if a scientist is interested in performing durability testing.

As other examples, the system and method enables users to perform multiple tests simultaneously (e.g., performing a frequency sweep simultaneously with a temperature ramp), to automatically pause and continue a test, or to dynamically change tests or test parameters during a testing process. Using looping and other scripting mechanisms, users can use feedback of raw data during one particular test to modify the parameters of a subsequent test that is to be performed within the same method.

The system and method also provides significant convenience and organization for users who wish to create incremental changes and additions to a core test procedure. The interface is capable of "encapsulating" a plurality of procedures within a single method, which can then be associated with a drag-and-drop icon for easy reuse.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for dynamically controlling operation of a rheometer system, comprising:

creating a program on a programming interface for executing a test upon a sample in a rheometer by receiving user selections of a plurality of nodes and connections of each node to another node according to directional connection indicators, wherein nodes indicate steps for performing a test upon a sample or configuring a rheometer for performing a test upon a sample;

identifying parameters associated with each selected node and receiving respective parameter values from a user;

creating scripts for generating a sequence of instructions to the rheometer, wherein the scripts include instructions for performing steps indicated by each of the selected nodes and in accordance with the directional connection indicators, wherein the scripts are generated in accordance with the selected parameter values;

downloading low-level instructions from the scripts for execution in the rheometer; and instructing drivers in the rheometer to perform the downloaded instructions, wherein the rheometer system is configured to enable one or more of dynamically changing rheology tests during a testing process, dynamically changing testing parameters during a testing process, and performing multiple rheology tests simultaneously.

2. The method of claim 1, wherein the programming interface is a graphical user interface enabling a user to select pre-existing icons or create icons representative of nodes.

3. The method of claim 1, further comprising a step of generating forms for prompting a user to enter, confirm, or modify parameter values, wherein each parameter corresponds to a field in a given form.

4. The method of claim 1, wherein scripts are created in accordance with information retrieved from a node class library, which tracks parameters associated with nodes and connections between nodes.

5. The method of claim 1, wherein certain nodes are dynamically created, further comprising a step of determining parameters to be identified for each dynamically created node.

6. The method of claim 1, wherein a sequence engine in the rheometer receives the scripts for executing the instructions independently of the programming interface.

7. The method of claim 6, wherein the scripts are downloaded to the rheometer via a TCP/IP connection for operation without further intervention from the programming interface.

8. The method of claim 1, wherein certain selected nodes are representative of a plurality of other nodes connected by directional connection indicators for grouping instructions associated with a test to be performed in the rheometer.

9. The method of claim 1, wherein the programming interface includes a chart for enabling a user to graphically select and drag icons from a palette.

10. The method of claim 1, wherein the programming interface includes a tree view for hierarchical navigation through selected nodes.

11. The method of claim 1, wherein the programming interface includes both a chart for enabling a user to graphically select and drag icons from a palette and a tree view for hierarchical navigation through selected nodes, and any change to either the chart or tree automatically results in corresponding change in the tree or chart, respectively.

12. A method for dynamically creating test sequences for a rheometer system, comprising:

selecting a plurality of nodes, wherein the nodes indicate steps for performing a test upon a sample or for configuring a rheometer for performing a test upon a sample;

connecting each node to another node according to directional connection indicators;

selecting parameter values associated with particular nodes, and when parameter values for a first node depend upon results of a second node, connecting the first and second node according to data flow indicators, wherein the rheometer system enables one or more of dynamically changing rheology tests during a testing process, dynamically changing testing parameters during a testing process, and performing multiple rheology tests simultaneously.

13. The method of claim 12, wherein scripts are created for generating a sequence of instructions to the rheometer indicated by each of the selected nodes and in accordance with the directional connection indicators and data flow indicators.

14. The method of claim 13, wherein low-level instructions are downloaded from the scripts for instructing drivers in the rheometer for performing the downloaded instructions.

15. The method of claim 13, wherein certain selected nodes are representative of a plurality of other nodes connected by directional connection indicators for grouping instructions associated with a test to be performed in the rheometer.

16. The method of claim 12, wherein nodes are selected by dragging icons from a palette in a graphical user interface.

17. A method for dynamically configuring a rheometer system to perform customized testing, comprising:

providing a programming interface for receiving user selections of a plurality of nodes and connections of each node to another node according to directional and data flow connection indicators, wherein nodes indicate steps for performing a test upon a sample or configuring a rheometer for performing a test upon a sample;

identifying parameters associated with each selected node and receiving respective parameter values from a user;

creating scripts for generating a sequence of instructions to the rheometer corresponding to programs created in the programming interface; and downloading low-level instructions from the scripts to the rheometer, wherein the rheometer is configured to execute low level instructions in a program sequence engine for operating drivers in the rheometer, wherein the rheometer system enables one or more of dynamically changing rheology tests during a testing process, dynamically changing testing parameters during a testing process, and performing multiple rheology tests simultaneously.

18. The method of claim 17, wherein the programming interface is a graphical user interface by which nodes can be selected from a palette through a drag-and-drop graphical display.

19. The method of claim 17, wherein scripts are created in accordance with values and parameters associated with nodes and maintained in a node class library.

20. The method of claim 17, wherein the sequence engine in rheometer executes the instructions independently of the programming interface.

21. The method of claim 20, wherein the scripts are downloaded to the rheometer via a TCP/IP connection for operation without further intervention from the programming interface.

22. A system for dynamically controlling operation of a rheometer, comprising:

a programming interface for executing a test upon a sample in a rheometer by receiving user selections of a plurality of nodes and connections of each node to another node according to directional connection indicators and by receiving respective parameter values associated with each node, wherein nodes indicate steps for performing a test upon a sample or configuring a rheometer for performing a test upon a sample;

a computer readable medium including a database memory configured to store test objects and test options used by the programming interface;

a scripts generator for generating a sequence of instructions to the rheometer, wherein the scripts include instructions for performing steps indicated by each of the selected nodes and in accordance with the directional connection indicators;

an output interface for downloading script files to a program sequence engine in a rheometer for executing low-level instructions for operating drivers in the rheometer wherein the system is configured for one or more of dynamically changing rheology tests during a testing process, dynamically changing testing parameters during a testing process, and performing multiple rheology tests simultaneously.

23. The system of claim 22, wherein the output interface additionally downloads instructions to an analysis and presentation tool for creating reports for display to a user.

24. The system of claim 22, wherein the programming interface operates on a graphical user interface for enabling selection of nodes and connections of nodes without requiring a user to enter programming code.

25. A method for dynamically controlling operation of a rheometer system, comprising:
creating a program on a programming interface for executing a test upon a sample in a rheometer by graphically selecting and positioning icons from a palette to a chart using a graphical user interface, wherein each icon indicates one or more steps for performing a test upon a sample or configuring a rheometer for performing a test upon a sample;
selecting parameters values for performing test steps, wherein parameters associated with each test step are presented in a plurality of dynamically generated forms; and
downloading low-level instructions for performing the indicated tests in accordance with the selected parameters for performance in the rheometer, wherein the rheometer system is configured for one or more of dynamically changing rheology tests during a testing process, dynamically changing testing parameters during a testing process, and performing multiple rheology tests simultaneously.

26. The method of claim 25, further comprising the step of encapsulating a sequence of steps for performing a test in a rheometer to be represented as a single icon.

27. A method for dynamically controlling operation of a rheometer system, comprising:
creating a program on a programming interface for executing a test upon a sample in a rheometer;
receiving user selections of a plurality of nodes and connections of each node to another node according to directional connection indicators, wherein nodes indicate steps for performing the test upon a sample or configuring a rheometer for performing the test upon a sample;
identifying parameters associated with each selected node and receiving respective parameter values from a user;
downloading low-level instructions for performing the programmed tests in the rheometer; and
downloading instructions for analyzing raw data to be input to a presentation and reporting interface from the rheometer, wherein the rheometer system is configured for one or more of dynamically changing rheology tests during a testing process, dynamically changing testing parameters during a testing process, and performing multiple rheology tests simultaneously.

28. A method for dynamically controlling operation of a rheometer system comprising:
a step for creating a program on a graphical instrument interface;
a step for receiving user selections of a plurality of nodes and connections of each node to another node according to directional connection indicators, wherein nodes indicate steps for performing the test upon a sample or configuring a rheometer for performing the g test upon a sample;
a step for identifying parameters associated with each selected node and receiving respective parameter values from a user;
a step for downloading instructions for performing tests according to the program; and
a step for converting raw data to rheological parameters, wherein the rheometer system is configured for one or more of dynamically changing rheology tests during a testing process, dynamically changing testing parameters during a testing process, and performing multiple rheolgy tests simultaneously.

* * * * *